United States Patent [19]

Morr et al.

[11] Patent Number: 4,689,407
[45] Date of Patent: Aug. 25, 1987

[54] 2-DEOXY-3-PHOSPHONYLMETHYL NUCLEOSIDES

[75] Inventors: Michael Morr, Wolfenbüttel; Christel Kakoschke, Lengede; Hans-Joachim Fritz, Cologne, all of Fed. Rep. of Germany

[73] Assignee: Gesellschaft für Biotechnologische Forschung mbH (GBF), Fed. Rep. of Germany

[21] Appl. No.: 585,643

[22] Filed: Mar. 2, 1984

[30] Foreign Application Priority Data

Mar. 4, 1983 [DE] Fed. Rep. of Germany ....... 3307744

[51] Int. Cl.$^4$ ............................................. C07H 15/12
[52] U.S. Cl. ..................................... 536/27; 536/28; 536/29
[58] Field of Search .............................. 536/27, 28, 29

[56] References Cited

U.S. PATENT DOCUMENTS 3,446,793  5/1969  Jones et al. ........................... 536/27

OTHER PUBLICATIONS

Harper's Review of Biochemistry, 18th Edition, 1981, p. 364.
Jones et al., Synthesis of Isosteric Phosphonate Analogs of Some Biologically Important Phosphodiesters, J Am Chem Soc 92, 5510 (1970a).
Jones et al., 3'-Deoxy-3'-(Dihydroxyphosphinylmethyl) nucleosides ..., J Am Chem Soc 92, 5511 (1970b).

Primary Examiner—Johnnie R. Brown
Assistant Examiner—F. T. Moezie
Attorney, Agent, or Firm—Kane, Dalsimer, Kane, Sullivan and Kurucz

[57] ABSTRACT

The invention relates to 2'-deoxy-3'-phosphonylmethyl nucleosides that are not substituted in the 2'-position.

8 Claims, 3 Drawing Figures

2-DEOXY-3-PHOSPHONYLMETHYL NUCLEOSIDES

Phosphinylmethyl derivatives of nucleosides which carry a hydroxy group in the 2'-position of the molecule are already known; see J. Am. Chem. Soc. 92 (1970) 5510.

The aim of the invention is to provide biologically active compounds which, inter alia, after customary modification and chemical incorporation into an oligonucleotide sequence and further incorporation into DNA, can no longer be cleaved by nucleases, especially by restriction enzymes. To this end, according to the invention 2'-deoxy-3'-phosphonylmethyl nucleosides of the following general formula are provided:

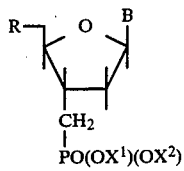

in which the following symbols have the following meanings:
B=adenine, $N^6$-benzoyladenine;
guanine, $N^2$-isobutyryl guanine, $N^2$-isobutyryl-4-O-(p-nitrophenyl ethyl)-guanine;
cytosine, $N^4$-benzoyl cytosine, 4-anisoyl cytosine;
thymine, 4-O-(p-nitrophenylethyl)-thymine; or uracil, and (a)

$X^1$, $X^2$=H, alkali metal, $NH_4$ or $C_{1-4}$-alkyl; or
$X^1$=chlorophenyl, 2,2,2-trichloroethyl or cyanoethyl and
$X^2$-triethylammonium
R=OH, $N_3$, $NH_2$, $NHR^1$, $NR^1R^2$, —O—PO(OY$^1$)-(OY$^2$),
—O—PS(OY$^1$)(OY$^2$),
—O—PO(OY$^1$)—O—PO(OY$^2$)(OY$^3$),
—O—PO(OY$^1$)—O—PO(OY$^2$)—O—PO(OY$^3$)-(OY$^4$)
$R^1$, $R^2$=$C_{1-4}$-alkyl, $C_{4-7}$-cycloalkyl, $C_{6-8}$-alkylaryl or $C_{6-8}$-arylalkyl, and
$Y^1$, $Y^2$, $Y^3$, $Y^4$=H, alkali metal or $NH_4$, or
R=5'-O-monomethoxytriphenylmethyl(5'-O-monomethoxytrityl) or 5'-O-(4,4'-dimethoxytriphenylmethyl) (5'-O-(4,4'-dimethoxytrityl)) or (b)

$X^1$=H, alkali metal, $NH_4$ or $C_{1-4}$-alkyl,
$X^2$ and R being absent with the formation of a ring of the grouping —PO(OX$^1$)—O—CH$_2$—.

(I) Manufacture of compounds of the general formula according to claim 1 in which the following symbols have the following meanings:
B=adenine, R=OH, $X^1$ and $X^2$=H, alkali metal or $NH_4$; or
B=adenine, R=OH, $X^1$ and $X^2$=$C_{1-4}$-alkyl; or
B=adenine, R=OH, $X^1$=H, alkali metal or $NH_4$ and $X^2$=$C_{1-4}$-alkyl.

DETAILED DESCRIPTION OF THE INVENTION

Figure 1:
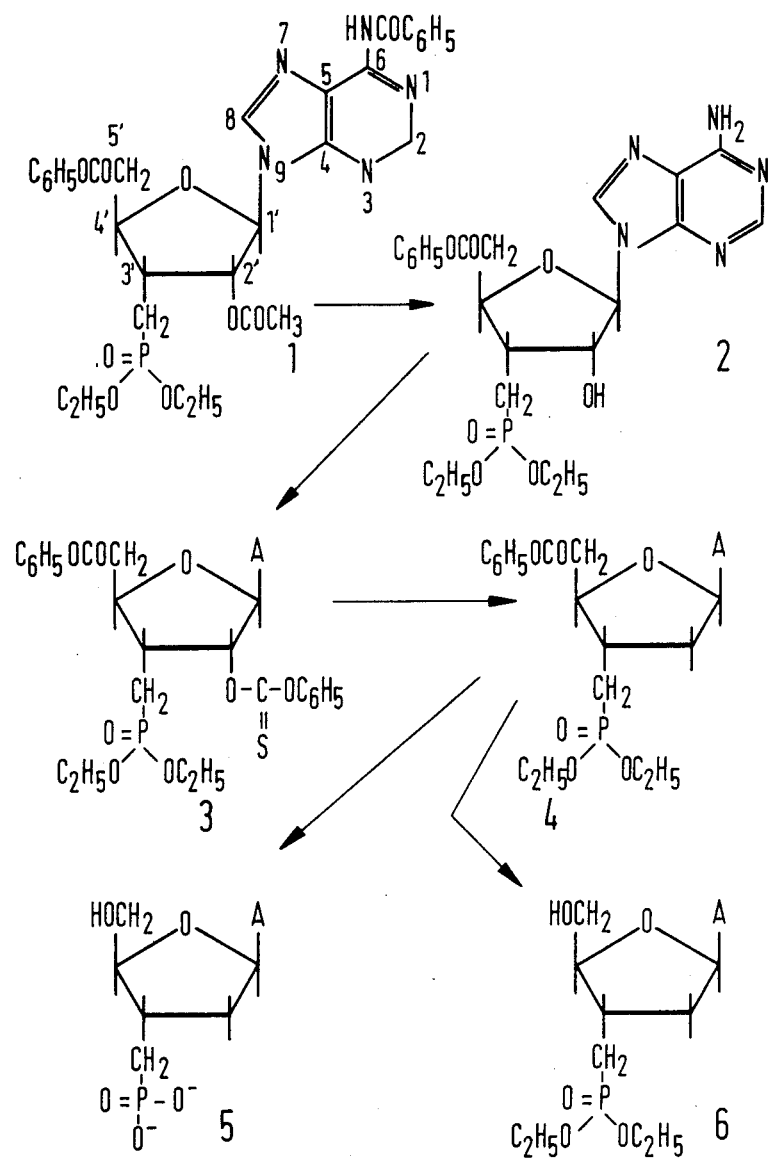
FIG. 1 is a schematic drawing of an embodiment synthesis of the invention as set forth in the examples.

The compounds according to the invention can be manufactured according to the invention by (a) using a compound of the general formula 1

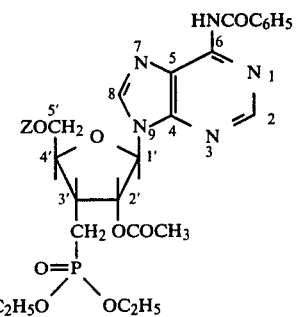

as starting material (Z=benzoyl or monomethoxytrityl), which has been obtained in accordance with Moffatt in the modification of Vorbrüggen [see J. Am. Chem. Soc. 92 (1970) 5511 and Chem. Ber. 114 (1981) 1279]. From this compound of the general formula 1 it is possible to remove selectively the acetyl group and the benzoyl group in the 6-position using an inorganic N-base or one of the salts thereof (for example with hydroxyammonium acetate in pyridine) in accordance with Ishido et al. [J. C. S. Perkin 1 (1979) 2088 or 1 (1980) 563].

(b) Subsequently the reaction product of the general formula 2

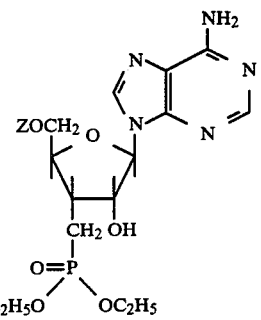

can be esterified with a compound of the formula $R^3$—CS—$R^4$ ($R^3$=Cl, $R^4$=phenyl, phenoxy; $R^3$=$R^4$=imidazol-1-yl) in the presence of 4-(dialkylamino)-pyridine (for example 4-(dimethylamino)-pyridine) in an organic solvent (for example dichloromethane) [see J. Org. Chem. 46 (1981) 4300 and 4843 and J. Am. Chem. Soc. 103 (1981) 932 and references].

(c) The resulting reaction product of the general formula 3

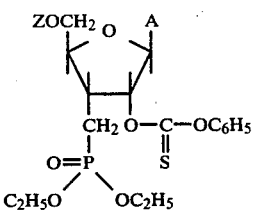

in which A represents an adenine radical, can be reduced with tributylin hydride in toluene, preferably at elevated temperature, especially in the range of from 30° to 90° C., for example at approximately 60° C.

(d1) The reaction product of the general formula 4

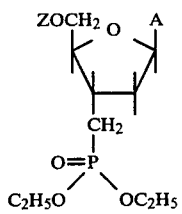

can be transesterified with halotrimethylsilane (such as bromo- or iodo-trimethylsilane) in a halogenated hydrocarbon (such as dichloromethane) and hydrolysed to form the free acid or its ammonium or alkali metal salt of the general formula of claim 1 (in which $X^1$ and $X^2$ represent a hydrogen atom, an alkali metal or NH$_4$ and R represents an OH group), or (d2) the mentioned protecting group Z (Z=benzoyl) can be removed from the reaction product of the general formula 4 with esterase (E.C.3.1.1.1) from pig's liver to form a diester of the general formula according to claim 1 ($X^1$ and $X^2$ representing a $C_{1-4}$-alkyl group and R representing an OH group), and, optionally, (d3) the diester can be hydrolysed to form a monoester of the general formula according to claim 1 ($X^1$ representing a hydrogen atom, an alkali metal or NH$_4$, $X^2$ representing a $C_{1-4}$-alkyl group and R representing an OH group).

Stage (a) can be carried out with a yield of from 60 to 70%, and stages (b), (c), (d1), (d2) and (d3) can be carried out with virtually quantitative yields. (II) Manufacture of compounds of the general formula according to claim 1 in which the following symbols have the following meanings:

B=adenine, R=N$_3$ and $X^1$ and $X^2$=$C_{1-4}$-alkyl; or

B=adenine, R=NH$_2$, NHR$^1$ or NHR$^2$ (R$^1$, R$^2$=$C_{1-4}$-aliphatic, $C_{4-7}$-cycloaliphatic, $C_{6-8}$-aliphatic/aromatic or $C_{6-8}$-aromatic/aliphatic radical), $X^1$=H, alkali metal or NH$_4$ and $X^2$=$C_{1-4}$-alkyl; or B=adenine, R=N$_3$, NH$_2$, NHR$^1$ or NR$^1$R$^2$ (R$^1$, R$^2$=$C_{1-4}$-aliphatic, $C_{4-7}$-cycloaliphatic, $C_{6-8}$-aliphatic/aromatic or $C_{6-8}$-aromatic/aliphatic radical) and $X^1$ and $X^2$=H, alkali metal or NH$_4$.

The compounds according to the invention can be manufactured according to the invention as follows:

(a) there is used as starting material a diester according to (I)(d2) which is activated in the 5'-position, for example with tosyl chloride (p-toluenesulphonic acid chloride) in pyridine.

(b1) Thereafter, the activated diester can be reacted with an azide, for example sodium azide, in dimethylformamide, to form a diester of the general formula according to claim 1 (B representing an adenosine radical, R representing an azide radical and R$^1$ and R$^2$ representing a $C_{1-4}$-alkyl radical); or (b2) the activated diester can be reacted with liquid ammonia or with a primary or secondary amine to form a semiester of the general formula according to claim 1 (B representing an adenosine radical, R representing an NH$_2$, NHR$^1$ or NR$^1$R$^2$ radical, R$^1$ and R$^2$ representing a $C_{1-4}$-aliphatic, $C_{4-7}$-cycloaliphatic, $C_{6-8}$-aliphatic/aromatic or $C_{6-8}$-aromatic/aliphatic radical, $X^1$ representing a hydrogen atom, an alkali metal or NH$_4$, and $X^2$ representing a $C_{1-4}$-alkyl radical); and, optionally, (b3) the resulting diester or semiester can be transesterified with a halotrimethylsilane (for example bromo- or iodo-trimethylsilane) and hydrolysed to form the free acid or one of the salts thereof of the general formula according to claim 1 (B representing an adenosine radical, R representing an N$_3$, NH$_2$, NHR$^1$ or NR$^1$R$^2$ radical, R$^1$ and R$^2$ representing a $C_{1-4}$-aliphatic, $C_{4-7}$-cycloaliphatic, $C_{6-8}$-aliphatic/aromatic or $C_{6-8}$-aromatic/aliphatic radical and $X^1$ and $X^2$ representing a hydrogen atom, an alkali metal or NH$_4$).

(III) Manufacture of compounds of the general formula according to claim 1 in which the following symbols have the following meanings:

B=adenine, R=—O—PO(OY$^1$)(OY$^2$), —O—PS-(OY$^1$)(OY$^2$), —O—PO(OY$^1$)—O—PO(OY$^2$)(OY$^3$) or —O—PO(OY$^1$)—O—PO(OY$^2$)—O—PO(OY$^3$)-(OY$^4$) (Y$^1$, Y$^2$, Y$^3$ and Y$^4$=H, alkali metal or NH$_4$) and $X^1$ and $X^2$=$C_{1-4}$-alkyl; or B=adenine, R=—O—PO(OY$^1$)(OY$^2$), —O—PS-(OY$^1$)(OY$^2$), —O—PO(OY$^1$)—O—PO(OY$^2$)(OY$^3$) or —O—PO(OY$^1$)—O—PO(OY$^2$)—O—PO(OY$^3$)-(OY$^4$) (Y$^1$, Y$^2$, Y$^3$ and Y$^4$=H, alkali metal or NH$_4$), $X^1$=H, alkali metal or NH$_4$ and $X^2$=$X^1$ or $C_{1-4}$-alkyl.

The compounds according to the invention can be manufactured according to the invention as follows:

(a) there is used as starting material a diester according to (I)(d2) which is phosphorylated according to Yoshikawa et al. [Tetrahedron Lett. (1967) 5065], for example with POCl$_3$ or PSCl$_3$ in a phosphoric acid trialkyl ester (such as triethyl phosphate) to form a diester of the general formula according to claim 1, and hydrolysed to form the free 5'-monophosphoric or 5'-thionophosphoric acid or salts thereof (B representing an adenosineradical, R representing a —O—PO(OY$^1$)-(OY$^2$) or —O—PS(OY$^1$)(OY$^2$) radical, Y$^1$ and Y$^2$ representing a hydrogen atom, an alkali metal or NH$_4$ and $X^1$ and $X^2$ representing a $C_{1-4}$-alkyl radical); and, optionally, (b) the resulting product is hydrolysed to form a semiester or to form free 3'-methylenephosphonic acid of the general formula according to claim 1 (B representing an adenosine radical, R representing a —O—PO(OY$^1$)(OY$^2$) or —O—PS(OY$^1$)(OY$^2$) radical, $X^1$, Y$^1$ and Y$^2$ representing a hydrogen atom, an alkali metal or NH$_4$ and $X^2$=$X^1$ or a $C_{1-4}$-alkyl radical); and, optionally.

(c) before or after step (b), the phosphoric acid obtained in stage (a) or its salt is phosphorylated according to Hoard & Ott [J. Am. Chem. Soc. 87 (1965) 1785] or Michelson [Biochim. Biophys. Acta, 1 (1964) 91] or enzymatically according to Marutsky (Diss. TU Braunschweig 1975), to form di- or tri-phosphoric acids or salts thereof of the general formula according to claim 1 (B representing an adenosine radical, R representing a —O—PO(OY$^1$)—O—PO(OY$^2$)(OY$^3$) or —O—PO(OY$^1$)—O—PO(OY$^2$)—O—PO(OY$^3$)(OY$^4$)

radical, $Y^1$, $Y^2$, $Y^3$ and $Y^4$ representing a hydrogen atom, an alkali metal or $NH_4$ and $X^1$ representing a hydrogen atom, an alkali metal, $NH_4$ or a $C_{1-4}$-alkyl radical, and $X^2$ representing a $C_{1-4}$-alkyl radical).

(IV) Manufacture of compounds of the general formula according to claim 1 in which the following symbols have the following meanings:

B=adenine, R and $X^2$ are absent with the formation of a ring of the grouping —PO($OX^1$)—O—$CH_2$—, $X^1$=H, alkali metal, $NH_4$ or $C_{1-4}$-alkyl.

The compounds according to the invention can be manufactured according to the invention as follows:

(a) there is used as starting material a diester according to (I)(d2) which is reacted with alkaline catalysts to form a compound of the general formula according to claim 1 (B representing an adenosine radical and $X^1$ representing a $C_{1-4}$-alkyl radical and R and $X^2$ being absent with the formation of a ring of the grouping —PO($OX^1$)—O—$CH_2$—); or (b) the free acid or one of its salts according to (I)(d1) is used as starting material and this starting compound (optionally in the form of its pyridinium salt) is cyclised with cyclisation agents (for example dicyclohexyl carbodiimide) in an organic solvent (for example pyridine) at elevated temperature; and, optionally, (c) the resulting product of stage (a) is transesterified with a halotrimethylsilane (for example bromo- or iodo-trimethylsilane) in a halogenated hydrocarbon (for example dichloromethane) and hydrolysed to form the free acid or salts thereof of the general formula according to claim 1 (B representing an adenosine radical and $X^1$ representing a hydrogen atom, an alkali metal or $NH_4$ and R and $X^2$ being absent with the formation a ring of the grouping —PO($OX^1$)—O—$CH_2$—.

Compounds of the general formula according to claim 1 in which B=guanine, cytosine, thymine or uracil can be manufactured by using as starting materials, instead of compounds of the general formula 2, corresponding compounds that carry a guanine, cytosine, thymine or uracil radical in the 1'-position.

(V) Manufacture of compounds of the general formula according to claim 1 in which the following symbols have the following meanings:

R=5'-O-monomethoxytrityl or 5'-O-(4,4'-dimethoxytrityl)

B=$N^6$-benzoyladenine; $N^2$-isobutyryl guanine, $N^2$-isobutyryl-4-O-(p-nitrophenylethyl)-guanine; 4-O-(p-nitrophenylethyl)-thymine; $N^4$-benzoyl cytosine or 4-anisoyl cytosine $X^1$=2-chlorophenyl, 2,2,2-trichloroethyl or cyanoethyl
$X^2$=triethylammonium These inventive compounds, for example compounds having the general formula 7

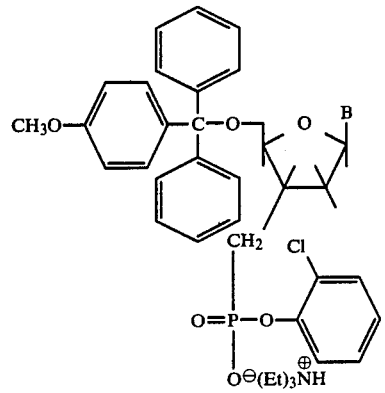

can be prepared as follows:

(a) A compound having the general formula 8 and prepared as described before under (I) where the protecting group Z has been cleaved in step (d2)

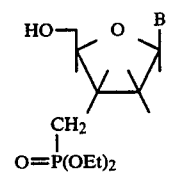

can be reacted with 4-monomethoxytriphenylmethyl-chloride(methoxytritylchloride) in the presence of 4-dimethylaminopyridine; cf. Y Lapidot and H. G. Khorana, J. Am. Chem. Soc. 85, 3862 (1963).

(b) The resulting compound having the general formula 9

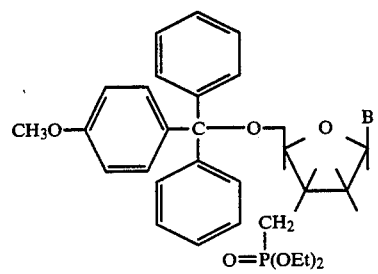

can be reacted with a halogenotrimethylsilane, viz.

(b1) with chlorotrimethylsilane in the presence of sodium iodide and acetonitrile according to T. Morita, Y. Okamoto and H. Sakurai, Tetrahedron Letters, No. 28, pages 2523 to 2526 (1978) or (b2) with bromotrimethylsilane according to C. E. McKenna, H. T. Higa, N. H. Higa and M. McKenna, Tetrahedron Letters, 977, (1977).

(c) The reaction product having the general formula 10

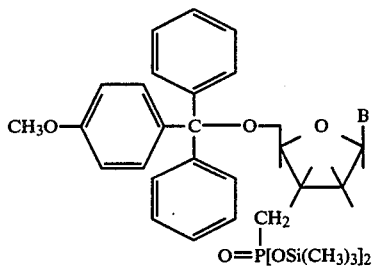

is hydrolized with methanol and subjected to a chromatography on DEAE-sephadex.

(d) The reaction product having the general formula 11

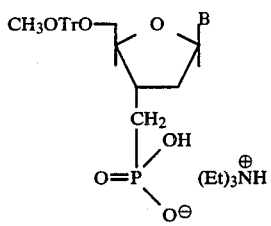

is then esterified in a manner known per se with 2-chlorophonol using 2,4,6-triisopropylbenzenesulfochloride in pyridine (activation) to obtain a compound having the general formula 7.

The inventive compounds can be used in connection with a really chemical synthesis of oligonucleotides according to the phosphotriester method:

The synthesis method was tested with isobutylphosphonic acid monoester of deoxyadenosine as model compound:

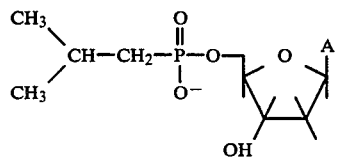

(alpha) isobutylphosphonic acid having the formula 13

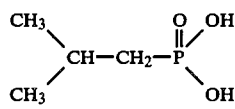

is reacted in a manner known per se with triisopropyl-benzenesulfochloride in pyridine with 2-chlorophenol and then subjected to a chromatography on DEAE-sephadex.

(beta) The reaction product having the formula 14

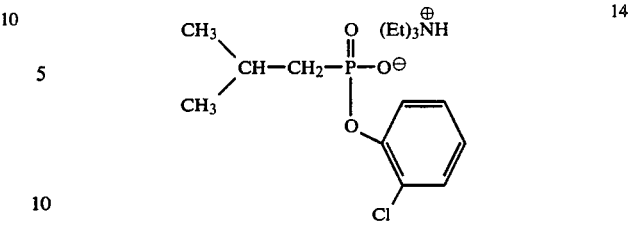

is reacted with MSNT (1-(mesitylenesulfonyl)-3-nitro-1,2,4-triazole) as condensation agent in pyridine and deoxy-3'-benzoyloxy-$N^6$-benzoyladenosine.

(gamma) The resulting mixed isobutylphosphonic acid diester having the formula 15

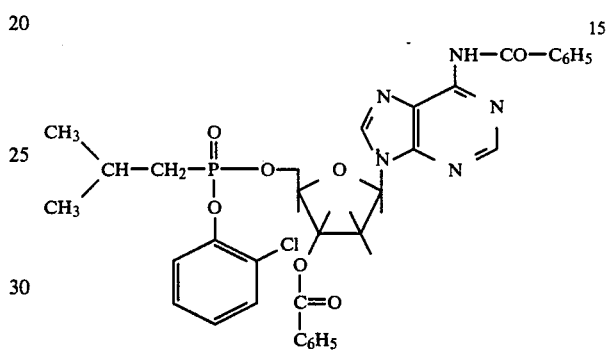

is hydrolized with concentrated ammonia to deoxyadenosineisobutylphosphonic acid monoester having the formula 12.

Figure 2:
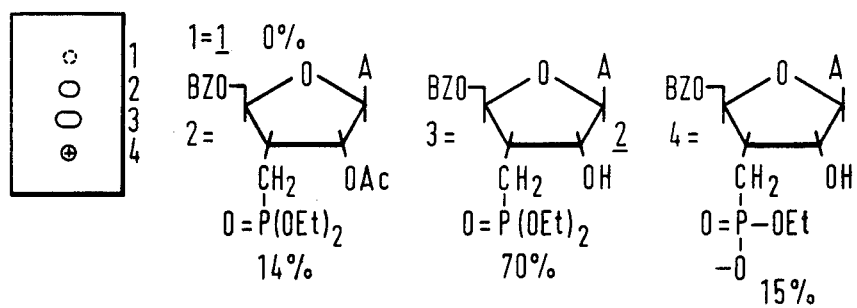
FIG. 2 is a representation of a thin-layer chromatogram and its interpretation, in reference to the examples.

The invention will be described in more detail in the following by way of examples with reference to the accompanying drawings of FIGS. 1 and 2 showing the structure of the compounds 1-6, referred to.

9-[5-O-Benzoyl-3-deoxy-3-(diethoxyphosphonylmethyl)-β-D-ribofuranosyl]-adenine or (5'-O-Benzoyl-3'-diethoxyphosphonylmethyl-3'-deoxyadenosine) (2)

1.134 g (1.74 mmol) of 1 are dissolved in 35 ml of pyridine with approximately 9 mmol of hydroxyammonium acetate ($NH_2OH \cdot HAc$) and are left to stand at room temperature for 45 hours.

Examination of a sample by thin-layer chromatography and subsequent evalution using a TLC-scanner gives the result shown in FIG. 2 of the accompanying drawings.

After removal of the volatile components (pyridine and excess hydroxyammonium acetate) under an oil pump vacuum, the residue is dissolved in chloroform/methanol 9:1 and introduced onto a column of silica gel (25×5 cm, silica gel 60, particle size 0.063–0.200 mm, Merck, Darmstadt). After elution with the same eluant and concentration by evaporation of the peak containing 2 there is obtained 580 mg (approximately 65%). Elution with methanol yields the semiester of 2.

9-[5-O-Benzoyl-3-deoxy-3-(diethoxyphosphonylmethyl)-2-O-phenoxythiocarbonyl-β-D-ribofuranosyl]-adenine (3) or
5'-O-Benzoyl-3'-diethoxyphosphonylmethyl-2'-O-phenoxy-thiocarbonyl-3'-deoxyadenosine 420 mg (0.83 mmol) of 2 are dissolved in 20 ml of anhydrous dichloromethane (Robins et al., operation in acetonitrile is not possible in the above case because the starting material crystallises out after a prolonged period) and, with the exclusion of moisture, 0.21 ml (1.5 mmol) of thiocarbonic acid O-phenyl ester chloride and 270 mg (2.2 mmol) of 4-dimethylaminopyridine are added. After stirring at room temperature for 12 hours, the reaction is complete (TLC, silica gel, eluant: dichloromethane/methanol 9:1). The mixture is concentrated to dryness and the residue is partitioned between ethyl acetate (EA) and 1M $KH_2PO_4$ solution (pH 4). After drying the EA phase with anhydrous sodium sulphate, it is concentrated to dryness and the residue is dissolved in a small quantity of dichloromethane/methanol 9:1 and chromatographed over a column of silica gel (10×5 cm). After concentration of the fraction containing 3 there is obtained 445 mg (67%).

9-[2-Deoxy-5-O-benzoyl-3-deoxy-3-(diethoxyphosphonyl-methyl)-β-D-ribofuranosyl]-adenine (4) or
5'-O-Benzoyl-3'-deoxy-3'-diethoxyphosphonylmethyl-2'-deoxyadenosine 190 mg (0.29 mmol) of 3 are dissolved in 6 ml of anhydrous toluene, and 0.155 ml of tributyltin hydride and 32 mg of 2,2'-azo-bis(2-methylpropionitrile) or (α,α-azo-isobutyronitrile) are added. After heating at 70° C. with the exclusion of moisture, the reaction is complete after 7 hours. After concentration to dryness the residue is dissolved in a small quantity of chloroform/methanol 9:1 and the solution is introduced onto a column of silica gel (24×2 cm). After elution with the above eluant, the peak containing 4 is concentrated. Yield: 123 mg (86%).

9-[2-Deoxy-3-deoxy-3-(dihydroxyphosphonylmethyl)-β-D-ribofuranosyl]-adenine or
2'-Deoxy-3'-dihydroxyphosphonylmethyl-3'-deoxyadenosine (5)

166 mg (0.34 mmol) of 4 are dissolved in 4 ml of anhydrous dichloromethane, and 0.27 ml (1.7 mmol) of trimethylbromosilane are added. The mixture is stirred overnight (in TLC, eluant: chloroform/methanol 9:1, starting material was no longer present) and concentrated in vacuo. The residue is hydrolysed with water, and the aqueous weakly acidic solution is concentrated to dryness. In order to remove the 5'-O-benzoyl protecting group, the residue is left to stand in saturated methanolic ammonia solution (25 ml) for 5 days. After evaporation to dryness the residue is dissolved in 10 ml of water, adjusted to pH 7.5, introduced onto a DEAE Sephadex column ($HCO_3$-form, 30×25 cm) and chromatographed with a gradient of 1 liter of water/1 liter of 0.4M TEAB buffer. After concentration of the peak containing 5 and repeated concentration by evaporation with methanol, the aqueous solution is introduced onto a Dowex sodium columnn and then lyophilised.

9-[2-Deoxy-3-deoxy-3-(diethoxyphosphonylmethyl)-β-D-ribofuranosyl]-adenine or
2'-Deoxy-3'-diethoxyphosphonylmethyl-3'-deoxyadenosine (6)

8 mg (16 μmol) of 4 are dissolved in 4 ml of water, and the solution is adjusted to pH 8.2 with saturated sodium bicarbonate solution. After the addition of 10 μl of esterase (Boehringer) the mixture is stirred for 24 hours at 37° C. while monitoring the pH value. The reaction is followed using thin layer chromatography (TLC, silica gel, eluant: chloroform/methanol 8:2). After concentration to dryness and extraction using the eluant, chromatography is carried out over a small column of silica gel. Yield: 5.2 mg (83%).

The structures of all compounds are ascertained accurately by $^1$H, $^{13}$C and $^{31}$P spectra and by chromatographic tests.

Abbreviations:
TLC=thin layer chromatography
TEAB buffer=triethylammonium bicarbonate buffer

We claim:
1. A 2'-deoxy-3'-phosphonylmethyl nucleoside of the formula

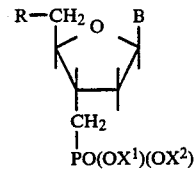

in which

B is attached to the C-1 carbon of the deoxyribose in the β configuration and is selected from the group consisting of adenine, $N^6$-benzoyladenine, guanine, $N^2$-isobutyryl guanine, $N^2$-isobutyryl-4-O-(p-nitrophenylethyl)-guanine, cytosine, $N^4$-benzoyl cytosine, 4-anisoyl cytosine, thymine, 4-O-(p-nitrophenylethyl)-thymine, and uracil, $X^1$ and $X^2$ are selected from the group consisting of H, alkali metals, $NH_4$ and $C_{1-4}$-alkyl; or $X^2$ is triethylammonium and $X^1$ is selected from the group consisting of chlorophenyl, 2,2,2-trichloroethyl and cyanoethyl, and R is selected from the group consisting of OH, benzoyl, $N_3$, $NH_2$, $NHR^1$, $NR^1R^2$, $-O-PO(OY^1)(OY^2)$, $-O-PS(OY^1)(OY^2)$, $-O-PO(OY^1-)-O-PO(OY^2)(OY^3)$, and $-O-PO(OY^1-)-O-PO(OY^2)-O-PO(OY^3)(OY^4)$ in which $R^1$ and $R^2$ are selected from the group consisting of $C_{1-4}$-alkyl, $C_{4-7}$-cycloalkyl, $C_{6-8}$-alkylaryl and $C_{6-8}$-arylalkyl, and $Y^1Y^2$, $Y^3$ and $Y^4$ are selected from the group consisting of H, alkali metals and $NH_4$, or R is selected from the group consisting of 5'-O-monomethoxytriphenylmethyl and 5'-O-(4,4'-dimethoxytriphenylmethyl).

2. A nucleoside according to claim 1, in which B is selected from the group consisting of adenine, $N^6$-benzoyladenine, guanine, $N^2$-isobutyryl guanine, cytosine, $N^4$-benzoyl cytosine, 4-anisoyl cytosine, thymine and uracil.

3. A nucleoside according to claim 1, in which $X^1$ and $X^2$ are selected from the group consisting of H and $C_{1-4}$-alkyl.

4. A nucleoside according to claim 1, in which $X^2$ is triethylammonium and $X^1$ is selected from the group consisting of chlorophenyl, 2,2,2-trichloroethyl and cyanoethyl.

5. A nucleoside according to claim 4, in which R is selected from the group consisting of 5'-O-monomethoxytriphenylmethyl and 5'-O-(4,4'-dimethoxytriphenylmethyl.

6. A nucleoside according to claim 4, in which R is selected from the group consisting of benzoyl, $-O-PO(OY^1)(OY^2)$, $-O-PO(OY^1)-O-PO(OY^2)(OY^3)$, and $-O-PO(OY^1)-O-PO(OY^2)-O-PO(OY^3)(OY^4)$ in which Y$^1$, Y$^2$, Y$^3$ and Y$^4$ are selected from the group consisting of H, alkali metals and NH$_4$.

7. A nucleoside according to claim 1, in which B is selected from the group consisting of adenine, guanine, cytosine and thymine.

8. A nucleoside according to claim 7, in which $X^1$ and $X^2$ are selected from the group consisting of H, alkali metals and NH$_4$.

* * * * *